US005660741A

United States Patent [19]

Suzuki et al.

[11] Patent Number: 5,660,741
[45] Date of Patent: Aug. 26, 1997

[54] PROCESS FOR PREPARATION OF SMALL GLASS ELECTRODE

[75] Inventors: Hiroaki Suzuki; Akio Sugama; Naomi Kojima, all of Kawasaki, Japan

[73] Assignee: Fujitsu Ltd., Kawasaki, Japan

[21] Appl. No.: 463,925

[22] Filed: Jun. 5, 1995

Related U.S. Application Data

[62] Division of Ser. No. 803,433, Dec. 6, 1991, Pat. No. 5,417,837.

[30] Foreign Application Priority Data

Dec. 6, 1990 [JP] Japan ................ 2-400550
Jul. 5, 1991 [JP] Japan ................ 3-164750

[51] Int. Cl.⁶ .................. H01L 21/00; G01N 27/36
[52] U.S. Cl. .................. 216/97; 65/102; 156/654.1; 156/657.1; 156/659.11; 156/662.1; 204/420; 204/435; 216/39; 216/41; 216/99
[58] Field of Search .................. 204/420, 435; 65/102; 216/39, 41, 97, 99; 156/654.1, 657.1, 659.11, 662.1

[56] References Cited

U.S. PATENT DOCUMENTS

| 2,366,489 | 1/1945 | Cary et al. ................ 216/97 |
| 3,458,422 | 7/1969 | Proctor ................ 204/420 |
| 3,560,256 | 2/1971 | Abrams ................ 204/197 |
| 3,573,948 | 4/1971 | Tarnopol ................ 216/39 |
| 3,676,319 | 7/1972 | Kirsten ................ 204/435 |
| 4,282,079 | 8/1981 | Chang et al. . |
| 4,592,824 | 6/1986 | Smith et al. ................ 204/416 |
| 4,786,396 | 11/1988 | Yee et al. ................ 204/420 |
| 4,816,132 | 3/1989 | Kotani et al. ................ 204/420 |
| 4,842,712 | 6/1989 | Seshimoto et al. ................ 204/416 |
| 4,859,505 | 8/1989 | Nakayama et al. ................ 216/97 |
| 4,863,560 | 9/1989 | Hawkins ................ 216/99 |
| 4,874,499 | 10/1989 | Smith et al. ................ 204/420 |
| 4,975,175 | 12/1990 | Karube et al. ................ 204/403 |
| 5,160,361 | 11/1992 | Murata et al. ................ 65/102 |
| 5,183,550 | 2/1993 | Mattiessen ................ 204/415 |

FOREIGN PATENT DOCUMENTS

| 0 269 031 | 6/1988 | European Pat. Off. . |
| 0269031 A2 | 6/1988 | European Pat. Off. . |
| 58-180 936 | 10/1983 | Japan . |

OTHER PUBLICATIONS

U.S. Application No. 08/153,054, Suzuki et al., filed Nov. 17, 1993 Assignee Fujitsu Limited.

*Primary Examiner*—T. Tung
*Attorney, Agent, or Firm*—Staas & Halsey

[57] ABSTRACT

A small glass electrode and process for preparation thereof are disclosed. This small glass electrode is characterized in that said glass electrode, which has a bonded structure comprises a reference electrode composed of silver/silver chloride, a glass substrate having a pad embedded therein, said pad being composed of gold or platinum and circuit-connected to the reference electrode, and a silicon substrate having a (100) plane selectively etched by the anisotropic etching technique and comprising a groove for injecting an electrolyte composed of an aqueous solution containing chlorine such as KCl, or HCl, at least one hole for holding the electrolyte and a glass film formed in a portion corresponding to the reference electrode. By this structure, the small glass electrode can be easily manufactured at a low cost.

9 Claims, 10 Drawing Sheets

PROCESS FOR PREPARATION OF SMALL GLASS ELECTRODE

This application is a divisional of application Ser. No. 07/803,433, filed Dec. 6, 1991, now U.S. Pat. No. 5,417,837.

BACKGROUND OF THE INVENTION (1) Field of the Invention

The present invention relates to a small glass electrode and a process for the preparation thereof. More particularly, the present invention relates to a small glass electrode formed by utilizing a micro-machining technique and a process for the preparation thereof.

(2) Description of the Related Art

A glass electrode is easily usable as a sensor for determining the hydrogen ion ($H^+$) concentration in an aqueous solution, and is widely and generally used.

The determination of the $H^+$ concentration is required not only in ordinary chemical experiments but also in fermentation control and in the medical field.

Furthermore, a biosensor fabricated by combining a glass electrode with either enzymes or microorganisms can be used for determining various chemical compounds.

For example, glucose reacts with dissolved oxygen with the aid of a catalyst called glucose oxidase and is oxidized to gluconolactone. Changes of the $H^+$ concentration during this reaction are measured, and the glucose concentration can be determined from the changed quantities. According to a similar principle, the urea concentration can be determined.

In the glass electrode, the $H^+$ concentration is measured by utilizing the electroconductivity of glass. Namely, the phenomenon that when a glass film having a thickness of about 100 μm and an electrical resistance of several hundred MΩ is placed in a solution, a voltage difference is produced according to the pH value of the solution which is utilized.

Figure 1:
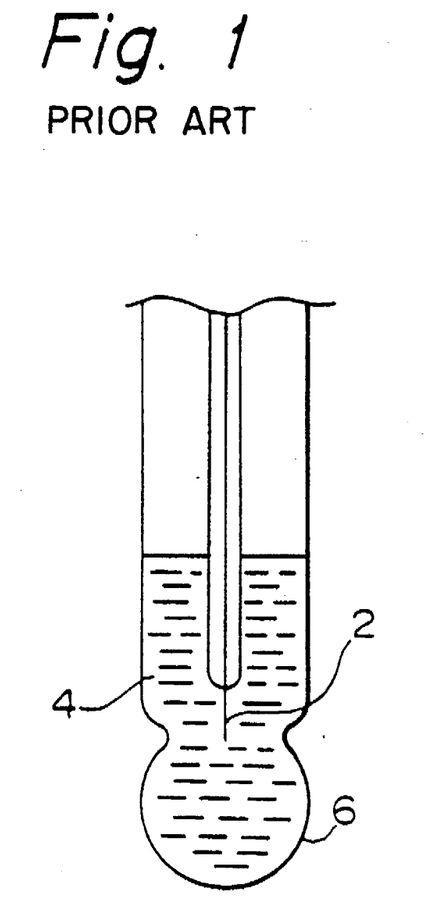
FIG. 1 is a cross sectional view of a conventional glass electrode.

FIG. 1 illustrates the structure of a sensing portion of a conventional glass electrode, which comprises a reference electrode 2 composed of silver or silver/silver chloride (Ag/AgCl), an internal solution 4 such as a potassium chloride (KCl) solution having a certain concentration, and a spherical sensing glass film 6 formed on the top end.

When this glass electrode is immersed in a solution containing $H^+$, in response to the active quantity (ai) of $H^+$, a potential is generated according to the Nernst equation:

$$E = \text{const} + (RT/F)\ln ai \quad (1)$$

wherein E represents the potential of the glass electrode, R represents the gas constant, T represents the absolute temperature, and F is the Faraday constant.
Accordingly, the $H^+$ concentration is determined by the above equation.

However, the commercially available glass electrode has a size similar to that of a fountain pen, as shown in FIG. 1, and the glass electrode is formed by glazing and it is expensive.

An ion-sensitive electric field effect transistor (abbreviated to "ISFET") has been developed as a small $H^+$ concentration sensor. Since a photolithographic technique of semiconductor production is utilized for its formation, the size thereof can be reduced.

In a device immersed in an aqueous solution, such as ISFET, insulation of the substrate is important.

Accordingly, many elements formed on a silicon (Si) substrate are diced into chips and a silicon nitride ($Si_3N_4$) film is formed on the peripheries of the chips to effect insulation, or an SOS (silicon-on-sapphire) substrate is used. Alternatively, there is adopted a method in which a thin film transistor (TFT) is formed on a glass substrate. However, the increased price of such a structure cannot be avoided and therefore, the sensor cannot be manufactured at a low price.

The conventional glass electrode formed by glazing is large size and expensive. In an ISFET formed by the photolithography of an Si substrate, insulation is indispensable and a price increase is inevitably caused by the necessity of maintaining the insulation, and reduction of the price is not easy.

Under this background, development of another method of providing a practical glass electrode of small size and low price is desired.

SUMMARY OF THE INVENTION

It is an object of the present invention to provide a small glass electrode capable of overcoming the foregoing problems and a process for the preparation thereof.

In accordance with one aspect of the present invention, this object can be attained by a small glass electrode, which has a bonded structure comprising a reference electrode composed of silver or silver/silver chloride, a glass substrate having a pad embedded therein, said pad being composed of gold or platinum and which is circuit-connected to the reference electrode, and a silicon substrate having a (100) plane selectively etched by the anisotroic etching technique and comprising a groove for injecting an electrolyte containing chlorine such as a potassium chloride buffer solution or hydrochloric acid solution, at least one reservoir for holding the electrolyte and a glass film formed in a portion corresponding to the reference electrode.

The glass film may have a multiple-layer (for example, two-layer) structure.

In accordance with another aspect of the present invention, there is provided a process for the preparation of a small glass electrode, which comprises selectively etching a glass substrate, forming a reference electrode, composed of silver or silver/silver chloride and a pad composed of gold or platinum and circuit-connected to the reference electrode, on the etched portion, subjecting a silicon substrate having a (100) plane as the substrate face to anisotropic etching to form an electrolyte-injecting groove and at least one electrolyte-holding reservoir therein, forming a glass film acting as a sensing film by utilizing a silicon oxide film as a mask, and bonding the formed glass substrate and silicon substrate to each other.

In accordance with still another aspect of the present invention, there is provided a process for the preparation of a small glass electrode, which comprises selectively etching a glass substrate and forming a reference electrode, composed of silver or silver/silver chloride and a pad composed of gold or platinum and circuit-connected to the reference electrode, on the etched portion, subjecting a silicon substrate having a (100) plane as the substrate face to anisotropic etching to form an electrolyte-injecting groove and at least one electrolyte-holding reservoir therein, removing the silicon oxide film which remains on the silicon substrate face, forming a glass film acting as a sensing film in a lower portion of the reservoir, and bonding the formed glass substrate and silicon substrate to each other.

The process of the present invention may further comprise a step of injecting the electrolyte into the reservoir from the injecting groove, according to need. Accordingly, a small glass electrode having an electrolyte injected in the reservoir is included within the scope of the present invention.

BRIEF DESCRIPTION OF THE DRAWINGS

Objects as well as advantages of the present invention will be come clear from the following description of the preferred embodiments made with reference to the accompanying drawings; wherein.

DETAILED DESCRIPTION OF THE PREFERRED EMBODIMENTS

The present inventors already succeeded in providing a practical utilizable small Clark oxygen electrode by applying the micro-machining technique to an Si substrate (U.S. Pat. No. 4,975,175).

This small oxygen electrode is often used for medical treatment. In this case, the oxygen concentration is measured relative to the $H^+$ concentration, rather than the oxygen concentration alone.

Accordingly, practical utilization of a small glass electrode by using the micro-machining technique was tried.

The following plan describes said utilization by the present inventors:

(1) The size of the glass electrode, presently used as the $H^+$ concentration sensor and found to operate well, is reduced.

(2) At least one holding hole (i.e., a cavity or reservoir) formed by anisotropic etching of an Si substrate, is used as a vessel for storing an electrolyte.

(3) A glass film formed by heat oxidation or sputtering is used as a sensing film (sensing element) for responding to the $H^+$ concentration.

(4) A reference electrode is formed on a glass substrate, and the glass substrate and Si substrate are bonded and integrated by the anodic bonding method.

(5) A reference electrode composed of Ag/AgCl, a lead-in line and a pad are embedded in the glass substrate.

The glass substrate to be bonded to the Si substrate is required to adhere tightly to the Si substrate not only during the course of cooling from the anode bonding treatment temperature, that is, of about 250° C., to normal (i.e., ambient) temperature but also in the application atmosphere. For this purpose, it is required that (1) the glass substrate should have a thermal expansion coefficient approximately equal to that of Si, (2) the glass substrate should be composed of a glass material having a low softening point, and (3) the glass substrate should have a high resistance to thermal stress. In view of the foregoing, a heat resistant glass such as PYREX or lead glass is preferably used. This glass alone can be used as the substrate, or this glass can be used in a state bonded to other glass substrates or an Si substrate.

Under this background, a glass electrode is formed by using the micro-machining technique according to the present invention.

In the glass electrode of the present invention, a thin glass film acting as the sensing film is formed by utilizing at least a part of an $SiO_2$ film obtained by wet oxidation of a wafer.

However, when a glass film having an increased strength is desired, the above-mentioned embodiment of the process for preparing a glass electrode is adopted in the present invention.

The thickness of the $SiO_2$ film formed by the wet oxidation of the silicon wafer is of about 1 μm in thickness, at the greatest, and it is impossible to increase the film thickness. Accordingly, in the process of the above-mentioned embodiment, a glass substrate is etched in advance to form a glass film having a desired thickness, a silicon oxide film remaining on the surface of the silicon substrate is removed, and then, the glass film is bonded to the bottom portion of the holding hole (i.e., cavity or reservoir).

In the so-prepared glass electrode of the second embodiment of the present invention, the strength of the glass film acting as the sensing film is increased. Therefore, the yield is improved and the glass electrode can be used without breaking.

In the glass respective electrodes obtained according to the above-mentioned two embodiments of the present invention, the sensitivity to the $H^+$ concentration is in practice sufficiently high. However, when a glass electrode having a further enhanced sensitivity is desired, a glass electrode having a structure described below can be adopted.

The voltage generated at the glass electrode is generally represented by the following Nernst equation:

$$E = \text{constant} - 0.059 pH \quad (1)$$

However, this equation is a theoretical formula, and it is not easy to construct the glass electrode so that the potential in accordance with this equation is obtained.

When a sensing film is formed by using a heat resistant glass such as PYREX having a thickness of about 50 μm, the gradient coefficient −0.059 (−59 mV) of the Nernst equation is about −0.03 (−30 mV).

Therefore, the present invention improves the glass material.

Lithium (Li) glass, sodium-calcium (Na—Ca) glass and the like are known as suitable glass materials for a glass electrode. However, in view of the heat resistance and strength limitations thereof, these materials cannot be used as the sensing film for a small glass electrode. The reasons are as follows.

(1) A heat treatment at about 800° C. is necessary for bonding to the Si substrate, for which the heat resistance is insufficient.

(2) A considerable strain is left after heat bonding, which these glass materials cannot resist.

According to the present invention, a double-layer film, used as the sensing film, is obtained by forming a film of a glass material having excellent characteristics, such as a lithium glass or a sodium-calcium glass, by sputtering or vacuum deposition thereof on a film of a glass material which is insufficient as to the characteristics required for the sensing film, such as a Pyrex glass, whereby a glass electrode satisfying, substantially, the requirement of the Nernst equation can be obtained.

In the present invention, it is sufficient if at least one holding hole is formed. However, if a plurality of holding holes are formed and glass films are bonded thereto, the risk of breaking the glass film is effectively reduced.

In the process of the present invention, bonding of the glass substrate and the silicon substrate is accomplished, for example, by a method of heating and bonding both substrates, a method using an adhesive or an anodic bonding method. From a practical viewpoint, the anode bonding method is preferably adopted.

The present invention will now be described in detail with reference to the following examples that by no means limit the scope of the invention.

EXAMPLE 1

Figure 2A:
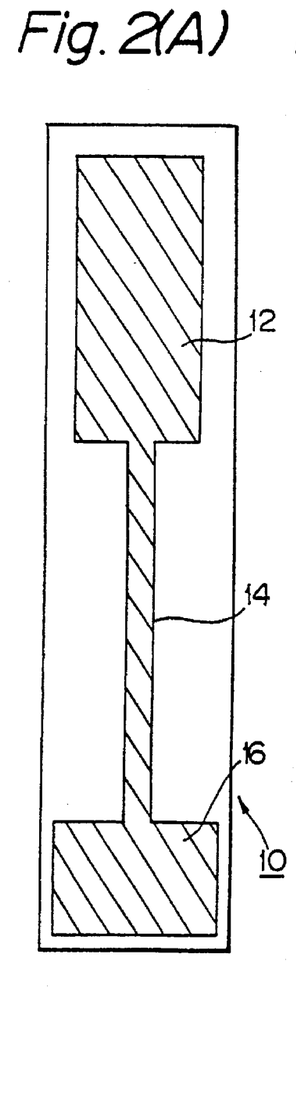
FIG. 2(A) is a planar view of a glass substrate in the glass electrode according to one embodiment of the present invention.
Figures 2B, 2C:
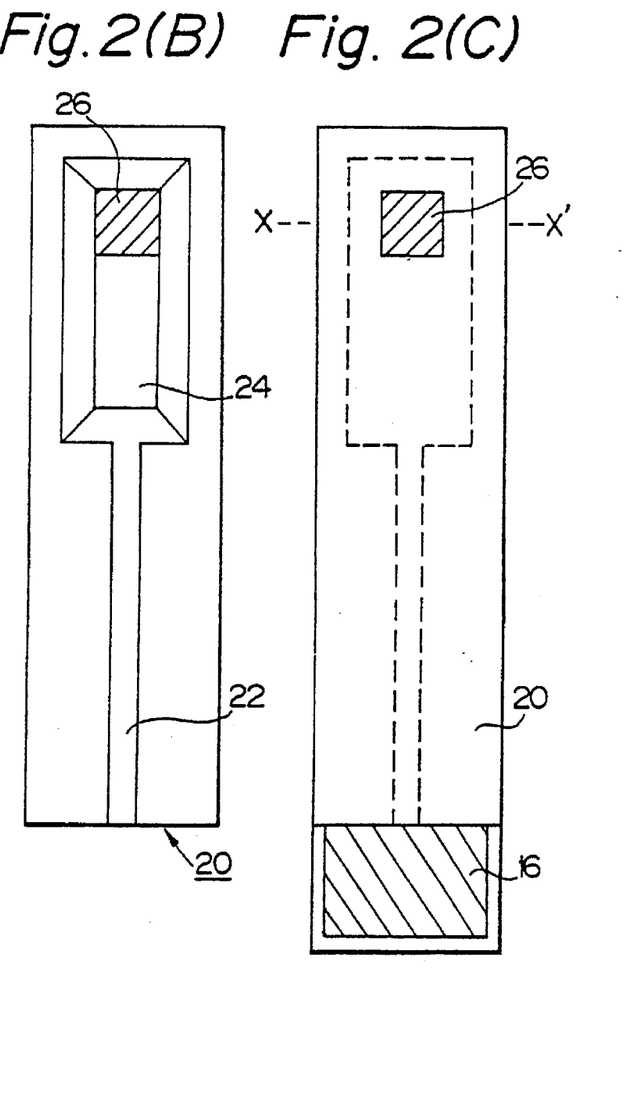
FIG. 2(B) is a planar view of an Si substrate of the glass electrode according to this embodiment.
FIG. 2(C) is a planar view of the glass electrode of this embodiment of the present invention, formed by bonding the glass substrate and Si substrate shown in FIGS. 2(A) and 2(B)

FIG. 2(A) is a planar view of a glass substrate 10 of the glass electrode according to one embodiment of the present invention, FIG. 2(B) is a planar view of an Si substrate 20 of the glass electrode according to this embodiment, and FIG. 2(C) is a planar view of the glass electrode of this embodiment of the present invention, formed by inverting and assembling the glass substrate onto the Si substrate 20 and bonding them.

A reference electrode 12 composed of silver or Ag/AgCl, a lead-in line 14 composed of Au and a pad 16 composed of Au are embedded in the glass substrate 10.

The substrate face of the Si substrate 20 is the (100) plane, and the Si substrate 20 is subjected to anisotropic etching, whereby a groove 22 for injecting an electrolyte, an electrolyte-holding hole (i.e., a cavity, or recess) 24 and a glass film 26 acting as the sensing film on at least a part of the hole 24 are formed. Incidentally, the groove only can also be made by the separate anisotropic etching.

In FIG. 2(C), the broken line indicates an interior glass electrode-forming region, and the pad 16 and glass film 26 appear on the side of the Si substrate 20.

Figure 3A:
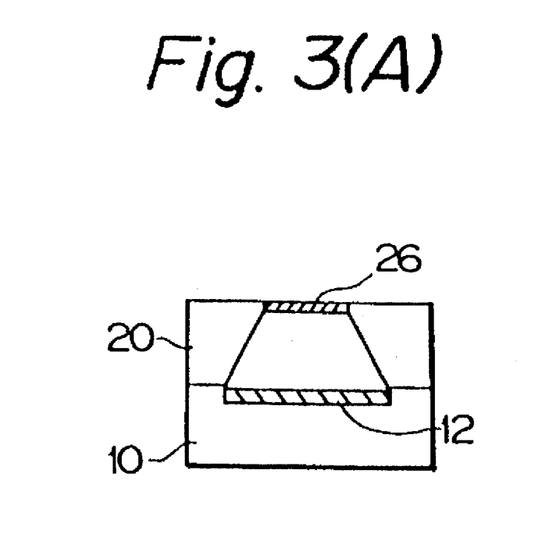
FIG. 3(A) is cross sectional view taken along line X–X' in FIG. 2(C) and FIG. 3(B) is a corresponding cross sectional view showing a modification of the glass electrode according to one embodiment of the present invention.

FIG. 3(A) is a view showing the section taken along X-X' in FIG. 2(C). As is seen from FIG. 2(C) and FIG. 3(A), the sensing film 26 is formed adjacent the bottom portion of the cavity, or reservoir of the etched Si substrate 20.

Figure 3B:
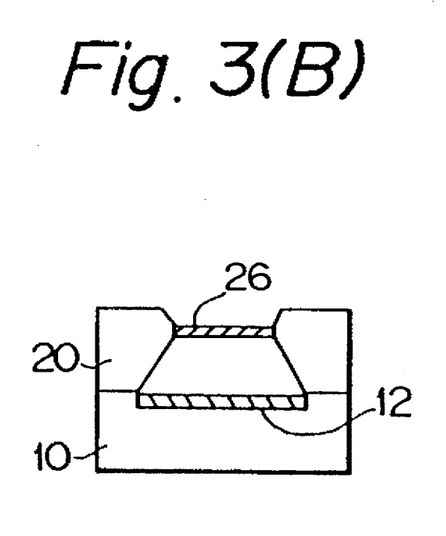

FIG. 3(B) is a sectional view showing a modification of this Example 1, where the Si substrate is etched also from the bottom so that the sensing film 26 is formed slightly on the inner side (i.e., on a recessed interior surface) of the Si substrate.

FIG. 4 is a diagram illustrating the steps of preparing the glass electrode of the present invention. One embodiment of the preparation process will now be described with reference to FIGS. 2(A)–2(C) and FIGS. 4(A)–4(F).

Formation of Glass Substrate:

A negative photoresist is spin-coated on the surface of a heat resistant glass such as PYREX substrate (Iwaki 7740) having a diameter of 2 inches and a thickness of 500 μm and is heated and dried at 150° C. for 30 minutes. Regions for formation of many reference electrodes 12, lead-in lines 14 and pads 16 are defined by corresponding windows in the photoresist and exposed by the photolithography, and the same resist is similarly coated and dried on the back surface.

Then, the glass substrate is immersed in a mixed solution comprising 50% hydrofluoric acid (HF), concentrated nitric acid ($HNO_3$) and ammonium fluoride (($NH_4)_F$) at a ratio of 1/1/8 for 80 minutes to etch the glass substrate to a depth of 3 μm. Then, the resist is peeled off by using a mixed solution comprising sulfuric acid ($H_2SO_4$) and hydrogen peroxide ($H_2O_2$) at a ratio of 2/1 (see FIG. 4(A)).

Then, the glass substrate 10 is sufficiently washed with a mixed solution of $H_2O_2$ and ammonia ($NH_4OH$) and pure water, and is then dried.

Then, an Au film is vacuum-deposited on the glass substrate 10. Since Au adheres very poorly to glass, a very thin chromium (Cr) film is vacuum-deposited on the glass substrate in advance to improve the adhesiveness.

The thickness of the Cr film is 400 Å and the thickness of the Au film is 4000 Å.

Then, a positive resist film (DFRP-5000 supplied by Tokyo Oka) is spin-coated, and the resist is coated on regions for forming reference electrodes 12, lead-in lines 14 and pads 16 by the photolithography. Then, the Au film and Cr film are selectively etched to form a reference electrode pattern comprising reference electrodes 12, lead-in lines 14 and pads 16.

The Au-etching solution is formed by dissolving 4 g of KI and 1 g of $I_2$ in 40 ml of water, and the Cr-etching solution is formed by dissolving 0.5 g of NaOH and 1 g of $K_3Fe(CN)_6$ in 4 ml of water.

Then, silver (Ag) is vacuum-deposited on the portion for forming the reference electrode 12, and in the same manner as described above, coating of a positive resist, heat-drying, light exposure and development are carried out to coat the resist only on the reference electrode-forming portion. Then, Ag etching is conducted and the resist is dissolved and removed, whereby a silver film is formed on the reference electrode-forming portion.

The Ag-etching solution is one comprising 29% $NH_4OH$, 31% $H_2O_2$ and pure water at a ratio of 1/1/20.

Then, the entire substrate is sufficiently washed with pure water and immersed in a 0.1M solution of $FeCl_3$ for 10 minutes to form a thin AgCl layer on the surface of Ag.

Figures 4A, 4B:
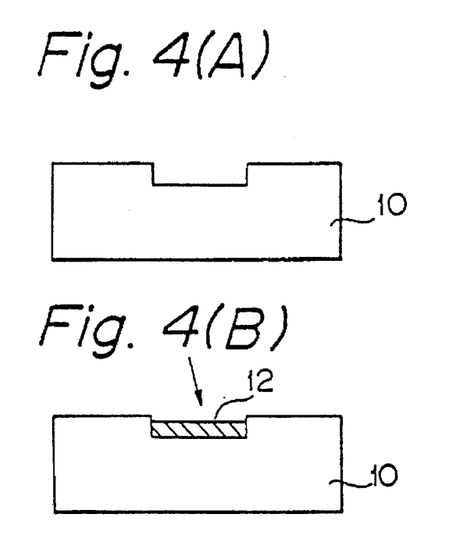
FIGS. 4(A) to 4(F) are diagrams illustrating steps of forming the glass electrode according to one embodiment of the present invention.

Then, the entire substrate is sufficiently washed with pure water to complete reference electrodes 12, lead-in lines 14 and pads 16 (FIG. 4(B)).

Formation of Si Substrate:

An Si substrate 20 having a (100) plane as the substrate face and having a thickness of 350 μm and a diameter of 2 inches is prepared, sufficiently washed with a mixed solution of $H_2O_2$ and $NH_4OH$ and pure water, and dried. The Si substrate 20 is subjected to wet oxidation at 1050° C. for 200 minutes to form an $SiO_2$ film 28 having a thickness of 1 μm on the entire surface.

Figures 4C, 4D:
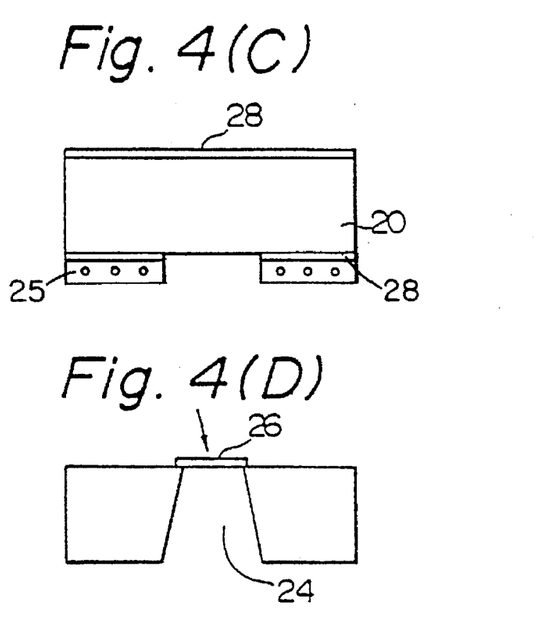

A negative resist (OMR-83 supplied by Tokyo Oka) having a viscosity of 60 cP is coated on the surface of the Si substrate, and light exposure, development and rinsing are carried out to form a resist pattern 25 see FIG. 4(C) on the substrate. Then, the Si substrate 20 is immersed in a mixed solution comprising 50% HF and 40% $NH_4F$ at a ratio of 1/6 and the exposed portion of $SiO_2$ 28 is etched and removed to expose an area for forming a holding hole 24 (see FIG. 4(C)) and 4(D).

Then, the resist film 25 shown in (FIG. 4(C)) is peeled off in a mixed solution comprising sulfuric acid and hydrogen peroxide at a ratio of 2/1. Then, the Si substrate 20 is immersed in 35% KOH at 80° C. and anisotropic etching of silicon is carried out to form the electrolyte-holding hole 24 in the reference electrode portion. (FIG. 4(D).

A glass film 26 acting as the sensing film is formed by patterning the $SiO_2$ film 28 the bottom portion of the holding hole (reservoir) 24 by utilizing adjacent the $SiO_2$ film 28 having a thickness of 1 μm, formed by wet oxidation.

If the $SiO_2$ 28 used as the mask is left on the surface of the Si substrate 20, a higher temperature is necessary for the anodic bonding. Therefore, $SiO_2$ other than the glass film 26 is completely removed by photolithography using a mixed solution comprising 50% HF and 40% $NH_4F$ at a ratio of 1/6. Thus, a vessel portion for storing an electrolyte is completed (see FIG. 4(D)).

Figure 4E:
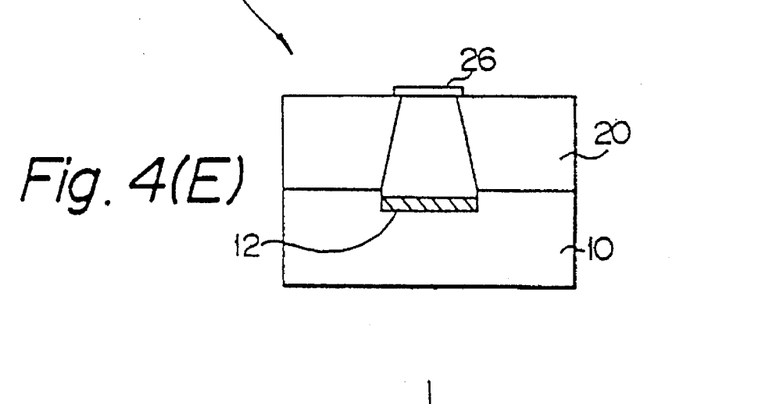

Bonding of Glass Substrate and Si Substrate:

The so-prepared glass substrate 10 and Si substrate 20 are immersed in pure water, sufficiently washed under ultrasonic vibrations and dried, and the substrates are bonded to each other by applying a voltage of 1200 V at a temperature of 250° C. across the substrates, with the Si substrate 20 located on the positive side and the glass substrate 10 located on the negative side, whereby the anodic bonding of the glass substrate and the silicon substrate is effected (see FIG. 4(E)).

Many glass electrode elements formed on the substrate are cut out into chips by using a dicing saw to obtain a small glass electrode.

When the so-obtained small glass electrode is used, an electrolyte is introduced into the interior of the electrode according to the following method.

A beaker is charged with 0.1M hydrochloric acid aqueous solution or an aqueous potassium chloride buffer solution contining a phosphoric acid (electrolyte), and the glass electrode is entirely immersed in the electrolyte and the entire system including the beaker is placed in a sealed vessel. Then, deaeration is carried out by a vacuum pump.

Figure 4F:
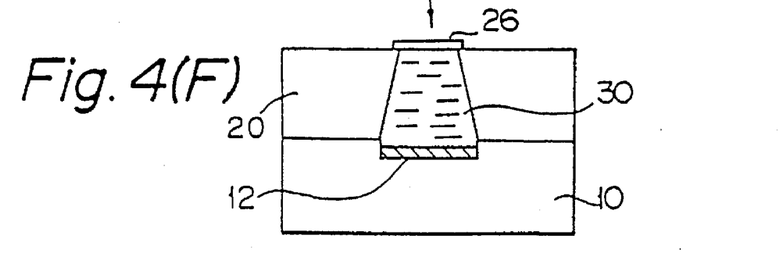

After bubbles have not come out of the groove 22 for injecting the electrolyte 30, air is introduced into the vessel. The hole can be filled with an epoxy regin.

By the above operation, the electrolyte is introduced into the inner space of the electrode, whereby a small glass electrode is obtained (see FIG. 4(F)).

According to this embodiment, a fine glass electrode can be prepared by using the micro-machining technique while maintaining a wafer-like shape. Accordingly, reduction of the device cost is possible.

Furthermore, since the glass electrode can be stored in a dry state, long-period storage is possible.

EXAMPLE 2

Another embodiment of the process for preparing the glass electrode of the present invention will now be described.

Figures 5A, 5B, 5C:
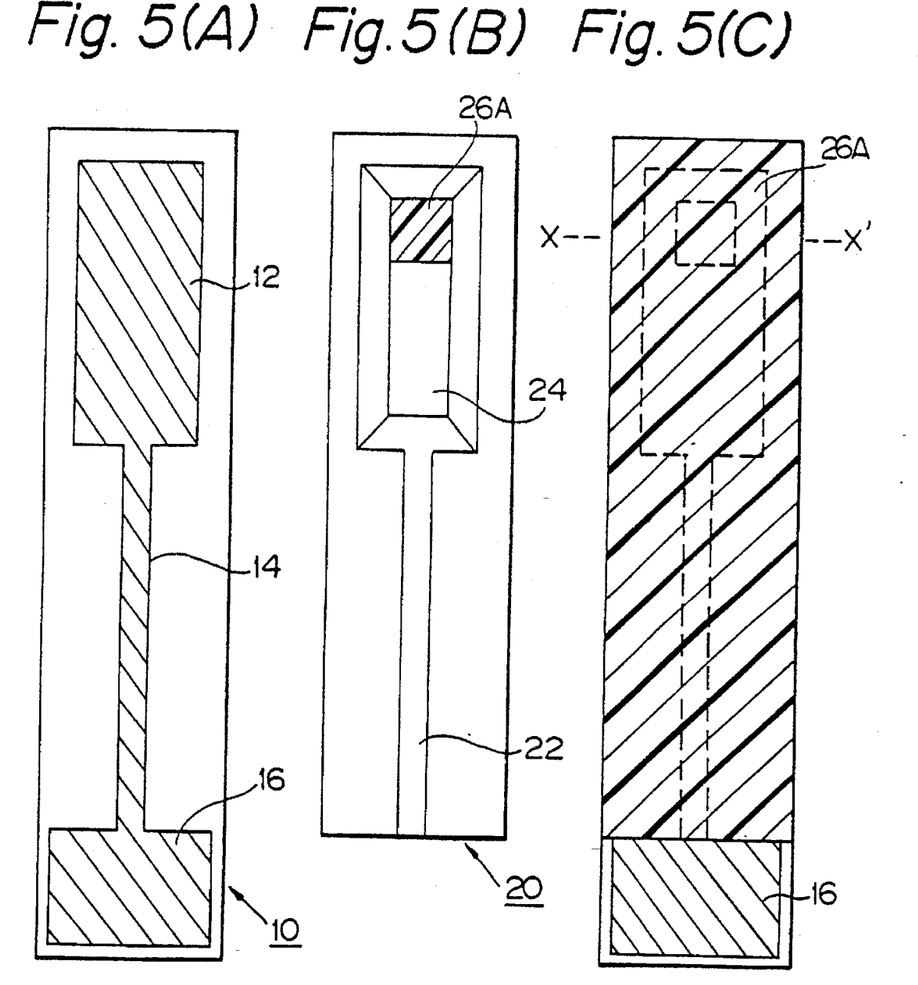
FIG. 5(A) is a planar view of a glass substrate in the glass electrode according to another embodiment of the present invention.
FIG. 5(B) is a planar view of an Si substrate of the glass electrode according to this embodiment.
FIG. 5(C) is a planar view of the glass electrode of this embodiment of the present invention, formed by bonding the glass substrate and Si substrate shown respectively in FIGS. 5(A) and 5(B)

FIG. 5(A) is a planar view showing a glass substrate of the glass electrode according to another embodiment of the present invention, FIG. 5(B) is a planar view of an Si substrate of the glass electrode according to this embodiment, and FIG. 5(C) is a planar view of the glass electrode of this embodiment of the present invention, formed by bonding the glass substrate and Si substrate shown respectively in FIGS. 5(A) and 5(B).

Figure 6:
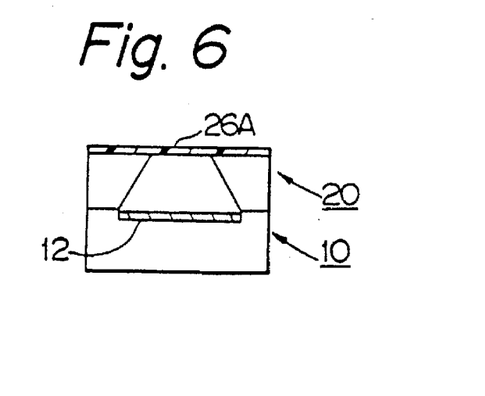
FIG. 6 is a cross sectional view taken along line X–X' in FIG. 5(C)

FIG. 6 is a cross-section taken along line X–X' in FIG. 5(C).

FIGS. 7(A) to 7(F) are diagrams illustrating steps of forming the glass electrode according to another embodiment of the present invention.

In FIGS. 5(A) through 7(F), the identical reference numerals represent the same members as in FIGS. 1 through 4 unless otherwise indicated.

The glass substrate-forming step is the same as described in Example 1. Accordingly, the description is omitted.

Furthermore, the Si substrate is prepared substantially in the same manner as described in Example 1, except that a part of the $SiO_2$ film is not utilized as the glass film acting as the sensing film, but the $SiO_2$ film is entirely removed.

Bonding of Glass Film to Si Substrate:

A heat resistant glass such as PYREX (Iwaki 774) is etched in a mixed solution comprising 50% HF and concentrated $HNO_3$ at a ratio of 2/1 to obtain a film having a thickness of about 50 μm, and the film is sufficiently washed to obtain a glass film 26 acting as the sensing film 26A.

Figure 7A:
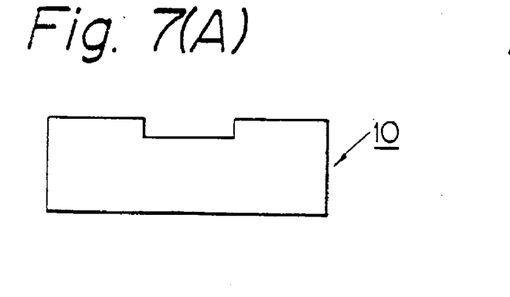
FIGS. 7(A) to 7(F) are diagrams illustrating steps of forming the glass electrode according to another embodiment of the present invention.
Figure 7B:
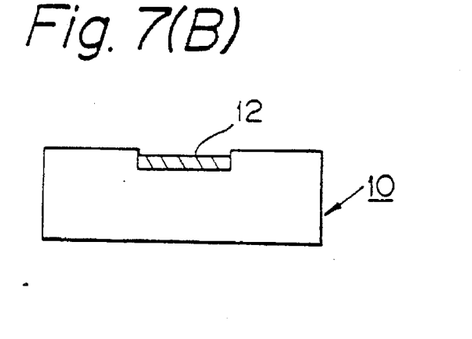
Figure 7C:
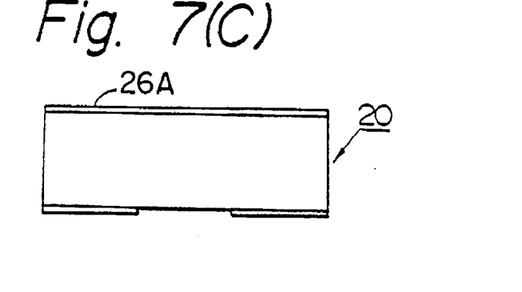
Figure 7D:
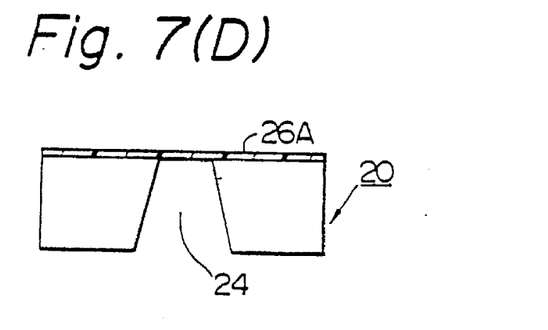

The glass film 26A is placed on the surface of the Si substrate 20, which is previously processed formed by perforating the Si substrate by the anisotropic etching to include the reservoir 24, and heated at 800° C. to effect bonding (see FIG. 7(D)).

Figure 7E:
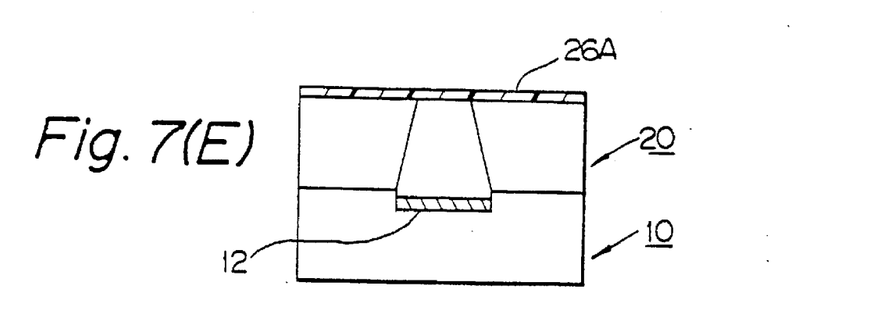
Figure 7F:
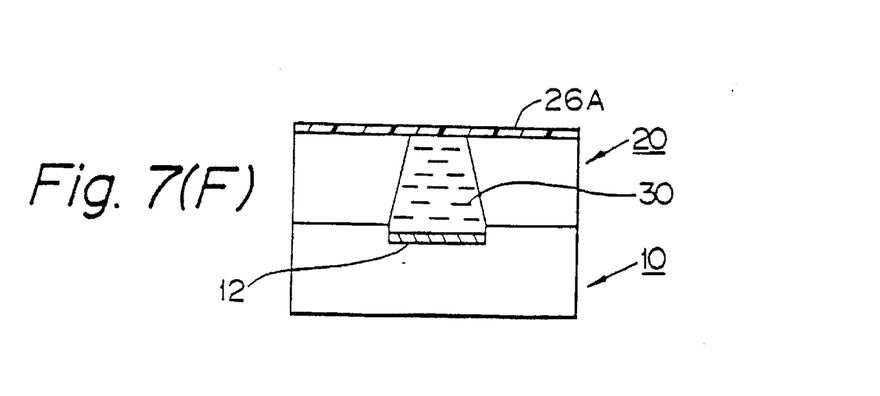

Bonding of the so-prepared glass substrate and Si substrate (FIG. 7(E)) and injection of the electrolyte (FIG. 7(F)) are carried out in the same manner as described in Example 1.

According to this embodiment of the present invention, the strength of the glass film of the formed glass electrode is increased and hence, the yield is increased, and the glass electrode is advantageous over the conventional glass electrode in that no breaking is caused during use.

EXAMPLE 3

Still another embodiment of the process for preparing the glass electrode of the present invention will now be described.

Figure 8A:
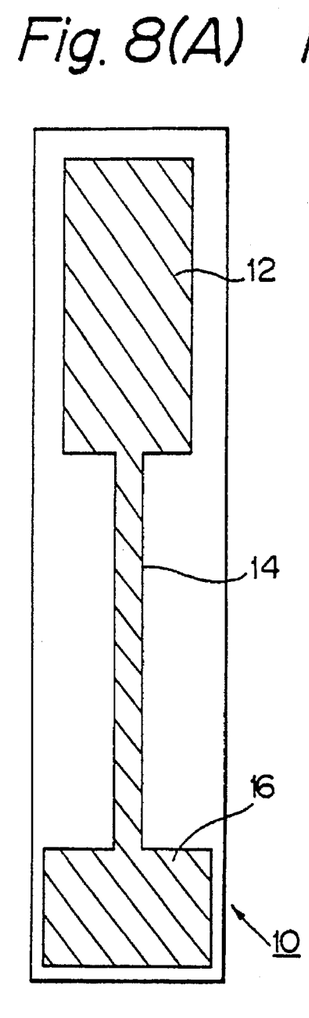
FIG. 8(A) is a planar view of a glass substrate in the glass electrode according to still another embodiment of the present invention.
Figure 8B:
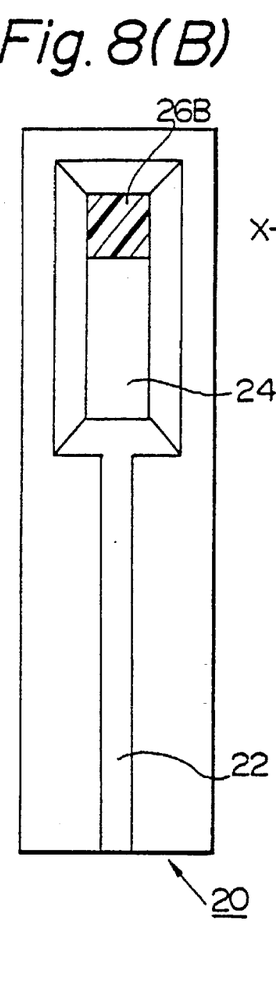
FIG. 8(B) is a planar view of an Si substrate of the glass electrode according to this embodiment.
Figure 8C:
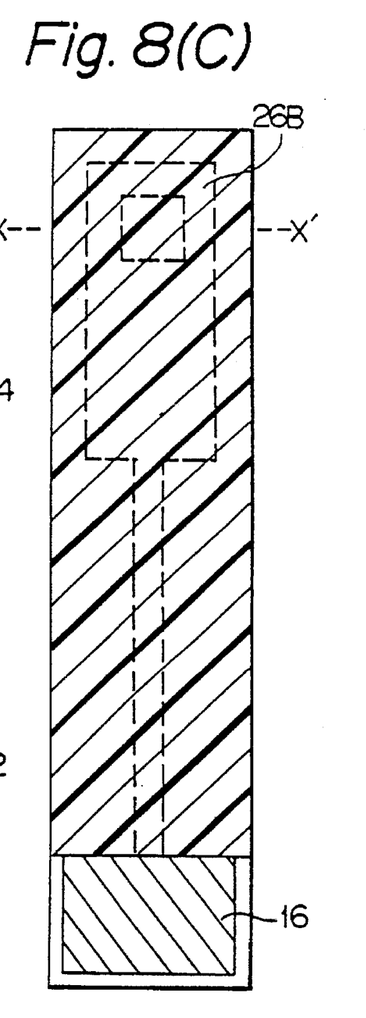
FIG. 8(C) is a planar view of the glass electrode of this embodiment of the present invention, formed by bonding the glass substrate and Si substrate shown respectively in FIGS. 8(A) and 8(B)

FIG. 8(A) is a planar view of a glass substrate of the glass electrode according to still another embodiment of the present invention, FIG. 8(B) is a planar view of an Si substrate of the glass electrode according to this embodiment, and FIG. 8(C) is a planar view of the assembled glass electrode of this embodiment of the present invention, formed by bonding the glass substrate respectively and Si substrate shown in FIGS. 8(A) and 8(B).

Figure 9:
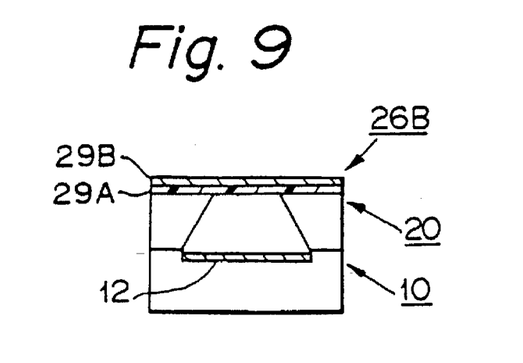
FIG. 9 is a cross-sectional view taken along line X–X' in FIG. 8(C)

FIG. 9 is a cross section taken along line X–X' in FIG. 8(C).

FIGS. 10(A) to 10(F) are diagrams illustrating steps of forming the glass electrode according to this embodiment of the present invention.

In FIGS. 8 through 10, identical reference numerals represent the same members as in FIGS. 1 through 4 unless otherwise indicated.

The glass substrate-forming step is the same as described in Example 1. Accordingly, the description is omitted.

Furthermore, the Si substrate is prepared substantially in the same manner as described in Example 1, except that a part of the SiO$_2$ film is not utilized as the glass film acting as the sensing film, but the SiO$_2$ film is entirely removed.

Bonding of Glass Film to Si substrate:

A heat resistant glass such as PYREX (Iwaki 7740) is etched in a mixed solution comprising 50% HF and concentrated HNO$_3$ at a ratio of 2/1 to obtain a film having a thickness of, for example, 20–150 μm, in this case 50 μm, and the film is sufficiently washed to obtain a first glass film 29A constituting a film 29A acting as the sensing film.

The first glass film 29A is placed on the back surface of an Si substrate 20 having a perforated or piercing holding hole (reservoir) 24 formed by anisotropic etching of an Si substrate and heated at 750° C. to effect bonding of the first glass film 29A to the Si substrate 20. Then, the Si substrate having the first glass film formed thereon is placed in at a sputtering device and an sodium-calcium Na—Ca glass is sputtered in a thickness of 500 nm to form a second glass film 29B on the first glass film 29A, whereby a glass film 26B acting as the sensing film is obtained (see FIG. 10(D)).

Figure 10A:
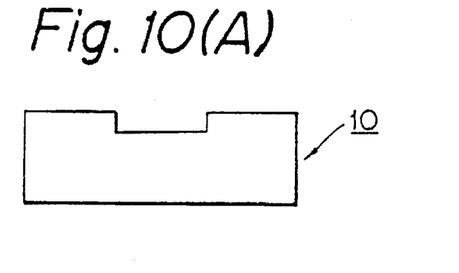
FIGS. 10(A) to 10(F) are diagrams illustrating steps of forming the glass electrode according to still another embodiment of the present invention.
Figure 10B:
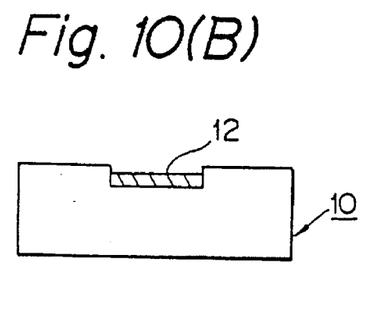
Figure 10C:
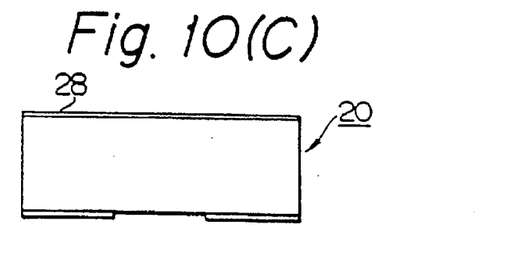
Figure 10D:
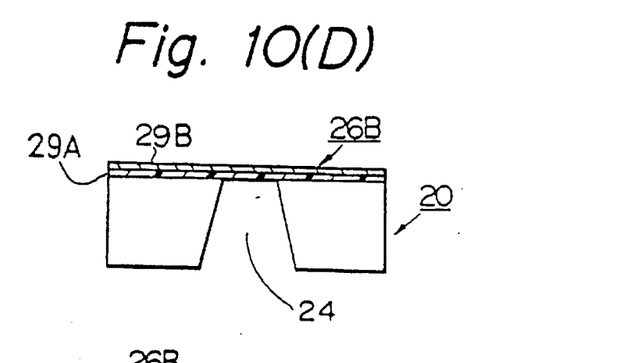
Figure 10E:
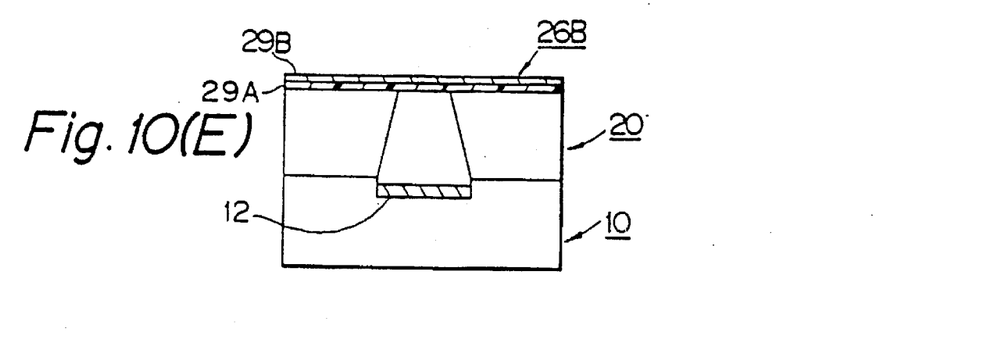
Figure 10F:
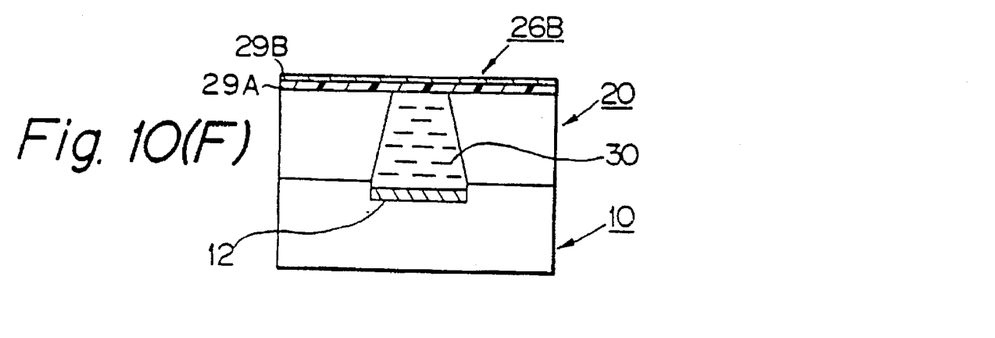

Bonding of the so-prepared glass substrate and Si substrate (FIG. 10(E)) and injection of an electrolyte (FIG. 10(F)) are carried out in the same manner as described in Example 1, whereby a double-layer small glass electrode is obtained.

The characteristics of the small glass electrode obtained in Example 3 are evaluated according to the following method.

The evaluation is performed by monitoring changes of the potential of the glass electrode relative to the potential of an external reference electrode of silver/silver chloride by using an electrometer. For examining changes of the potential relative to changes of the pH value, the sensing portion of the electrode is immersed in a 10 mM TRIS (Trimethyl aminomethane) solution, and HCl is added to reduce the pH value. At each pH value, the potential of the glass electrode is examined. The experiment is conducted at 25° C.

Figure 11:
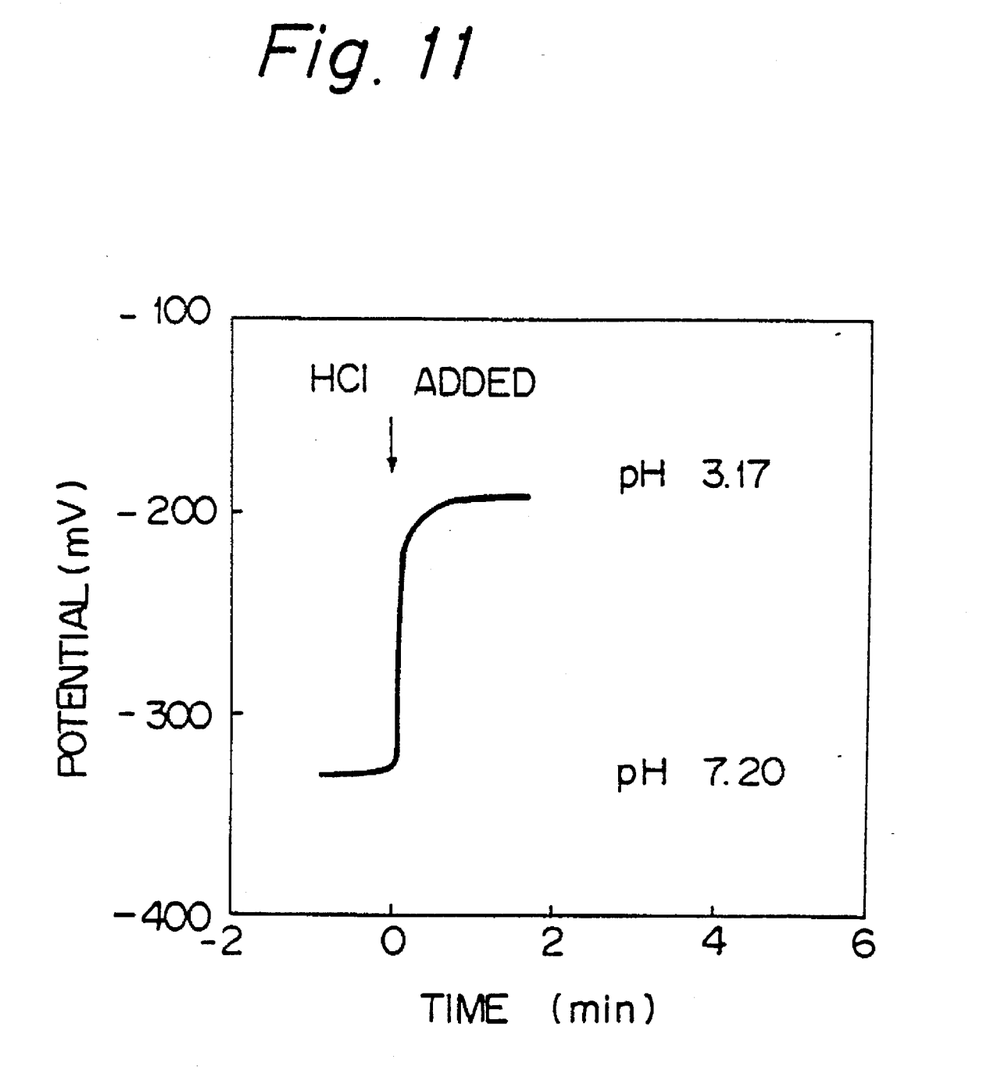
FIG. 11 is a diagram illustrating a response curve of the glass electrode of the present invention.

The response curve obtained when the pH value of the external buffer solution is changed is shown in FIG. 11.

Figure 12:
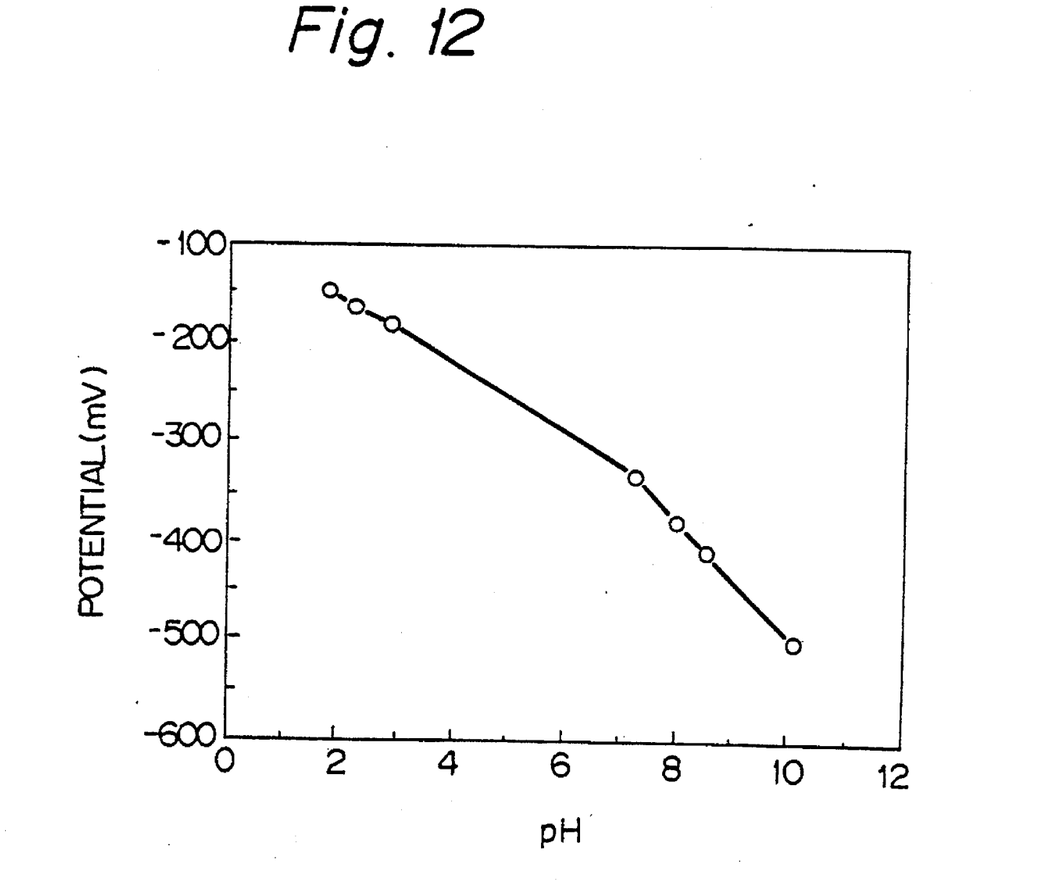
FIG. 12 is a curve illustrating the relation between the change of the $H^+$ concentration and the change of the electrode potential in the glass electrode of the present invention.

As is seen from FIG. 11, a very clear response curve is obtained. When the pH value is changed, the small glass electrode immediately shows a change and a 90% response time is 10 seconds. A change of the electrode potential observed when the pH value is changed is shown in FIG. 12. It is seen that a linear relation is established between them over a broad pH value range of from 2 to 10. The gradient of the linear relation is a value approximate to −59 mV/pH of the theoretical value of the Nernst equation at 25° C.

We claim:

1. A process for preparing a small glass electrode, comprising the steps of:
    selectively etching a glass substrate to form an etched portion on the surface of the glass substrate,
    forming a reference electrode composed of silver/silver chloride in a portion of said etched portion of said glass substrate such that the reference electrode is embedded to extend into the glass substrate,
    forming a pad composed of gold and circuit-connected to said reference electrode, in another portion of said etched portion of said glass substrate,
    anisotropically etching a first main surface of a silicon substrate having a (100) plane on said first main surface to form an electrolyte-injecting groove on said first main surface of said silicon substrate, and a hole extending from said first main surface to a second, opposite main surface of said silicon substrate, said groove being in communication with said hole and extending to an end of said silicon substrate, said anisotropical etching being carried out using a silicon oxide film as a mask,
    forming a glass film acting as a sensing film on said second main surface of said silicon substrate from said silicon oxide film, said glass film covering and closing said hole on said second main surface of said silicon substrate so as to form an electrolyte-holding hole, and
    bonding the glass substrate and the silicon substrate to each other to form a unitary structure, in such a way that said etched portion of said glass substrate and said first main surface of said silicon substrate face each other and said electrolyte-holding hole and electrolyte-injecting groove are substantially enclosed within the unitary structure.

2. A process according to claim 1, wherein said bonding is carried out by anodic bonding.

3. A preparation process according to claim 2, which further comprises a step of injecting an electrolyte from the electrolyte-injecting groove.

4. A preparation process according to claim 1, which further comprises a step of injecting an electrolyte from the electrolyte-injecting groove.

5. A process for preparing a small glass electrode, comprising the steps of:
    selectively etching a glass substrate to form an etched portion on the surface of the glass substrate,
    forming a reference electrode composed of silver/silver chloride in a portion of said etched portion of said glass substrate such that the reference electrode is embedded to extend into the glass substrate,
    forming a pad composed of gold and circuit-connected to said reference electrode, in another portion of said etched portion of said glass substrate,
    anisotropically etching a first main surface of a silicon substrate having a (100) plane on said first main surface to form an electrolyte-injecting groove on said first main surface of said silicon substrate, and a hole extending from said first main surface to a second, opposite main surface of said silicon substrate, said groove being in communication with said hole and extending to an end of said silicon substrate, said anisotropical etching being carried out using a silicon oxide film as a mask,
    removing the silicon oxide film from the silicon substrate,
    forming a glass film acting as a sensing film on said second main surface of said silicon substrate, said glass film covering and closing said hole on said second main surface of said silicon substrate so as to form an electrolyte-holding hole, and
    bonding the glass substrate and silicon substrate to each other to form a unitary structure, in such a way that said etched portion of said glass substrate and said first main surface of said silicon substrate face each other and said electrolyte-holding hole and electrolyte-injecting groove are substantially enclosed within the unitary structure.

6. A process according to claim 5, wherein said bonding is carried out by the anodic bonding.

7. A preparation process according to claim 6, which further comprises a step of injecting an electrolyte from the electrolyte-injecting groove.

8. A process according to claim 5, wherein said glass film acting as a sensing film is composed of an upper glass layer and a lower glass layer, the glass film being made of one of sodium-calcium glass and lithium glass with the upper glass layer being sputtered or vacuum deposited on the lower glass layer, the upper and lower glass layers having the same composition.

9. A preparation process according to claim 5, which further comprises a step of injecting an electrolyte from the electrolyte-injecting groove.

* * * * *